United States Patent [19]
Prescott

[11] Patent Number: 5,989,245
[45] Date of Patent: *Nov. 23, 1999

[54] METHOD AND APPARATUS FOR THERAPEUTIC LASER TREATMENT

[76] Inventor: Marvin A. Prescott, 833 Moraga Dr, Suite 15, Los Angeles, Calif. 90049

[*] Notice: This patent is subject to a terminal disclaimer.

[21] Appl. No.: 08/829,247

[22] Filed: Mar. 31, 1997

Related U.S. Application Data

[63] Continuation-in-part of application No. 08/215,263, Mar. 21, 1994, Pat. No. 5,616,140, which is a continuation-in-part of application No. 08/703,488, Aug. 26, 1996, Pat. No. 5,814,039.

[51] Int. Cl.$^6$ ........................................... A61B 17/36
[52] U.S. Cl. ................................... 606/14; 607/89
[58] Field of Search .................. 606/2, 3, 7, 10–14, 606/27, 28; 607/88, 89, 92; 604/20, 21

[56] References Cited

U.S. PATENT DOCUMENTS

| | | |
|---|---|---|
| 4,676,246 | 6/1987 | Korenaga . |
| 4,881,547 | 11/1989 | Danforth . |
| 4,915,108 | 4/1990 | Sun . |
| 4,930,504 | 6/1990 | Diamantopoulos et al. . |
| 5,000,752 | 3/1991 | Hoskin et al. . |
| 5,259,380 | 11/1993 | Mendes et al. . |
| 5,272,716 | 12/1993 | Soltz et al. . |
| 5,300,097 | 4/1994 | Lerner et al. . |
| 5,330,517 | 7/1994 | Mordon et al. ............................ 607/89 |
| 5,358,503 | 10/1994 | Bertwell et al. . |
| 5,370,615 | 12/1994 | Johnson . |
| 5,380,316 | 1/1995 | Aita et al. . |
| 5,395,361 | 3/1995 | Fox et al. . |
| 5,445,608 | 8/1995 | Chen et al. .............................. 604/20 |
| 5,470,352 | 11/1995 | Rappaport . |
| 5,505,726 | 4/1996 | Meserol . |
| 5,531,738 | 7/1996 | Hessel et al. ............................ 606/2 |
| 5,558,672 | 9/1996 | Edwards et al. ......................... 606/41 |
| 5,616,140 | 4/1997 | Prescott . |
| 5,620,439 | 4/1997 | Abela et al. ............................. 606/11 |
| 5,662,712 | 9/1997 | Pathak et al. ........................... 600/195 |
| 5,728,090 | 3/1998 | Martin et al. ........................... 606/3 |
| 5,741,246 | 4/1998 | Prescott ................................... 606/7 |

OTHER PUBLICATIONS

"GaInAsP/AlGaInP–Based Near–IR (780nm) Vertical–Cavity Surface–Emitting Lasers," by R.P. Schneider, Jr. et al., Electronics Letters, Mar. 30, 1995, vol. 31, No. 7, pp. 554–555.

"Laser Biostimulation of Healing Wounds: Specific Effects and Mechanisms of Action," by Chukuka S. Enwemeka, The Journal of Orthopaedic and Sports Physical Therapy, 1988, vol. 9, No. 10, pp. 333–338.

"Low Level Laser Therapy in Patients with Venous Ulcers: Early and Long–term Outcome," by Kleinman et al., Journal of Low Level Laser Therapy and Photobioactivation, Jul. 1996.

"Biomechanical Effects of Three Different Periods of GaAs Laser Photostimulation on Tenotomized Tendons," by Enwemeka et al., Journal of Low Level Laser Therapy and Photobioactivation, Jun. 1, 1994.

(List continued on next page.)

*Primary Examiner*—Michael Peffley
*Attorney, Agent, or Firm*—Graham & James LLP

[57] ABSTRACT

A powered portable laser bandage having one or many vertical cavity surface-emitting laser arrays embedded therein may be worn by a patient and applied to an area of the patient's body near the heart. The device supplies the patient with a preprogrammed laser therapy regimen. A physician programs the device and attaches the device to a patient who may then wear the device for several days without visiting a physician. The device is small enough to be worn under clothes and does not interfere with the patient's normal activities. The low-level laser energy promotes angiogenesis of the heart myocardium. Alternatively, the device may be adapted to be implanted into a skin surface of the patient, or provided in a catheter that is inserted in the vasculature system of the patient.

7 Claims, 7 Drawing Sheets

OTHER PUBLICATIONS

"Attenuation of the Process of Skeletal Muscle Regeneration by Low Energy Laser Irradiation," by Bibikova et al, Journal of Low Level Laser Therapy and Photobioactivation, Abstracts: Walt 1996, vol. 8, No. 1, Apr. 1996.

"Our Experience in the Use of a Low Intensity HeNe Laser in the Treatment of Acute Myocardial Infarction," by Kipshidze, Journal of Low Level Laser Therapy and Photobioactivation, Abstracts: Walt 1996, vol. 8, No. 1, Apr. 1996.

"Photochemotherapy in Clinical and Veterinary Medicine: Therapeutic Effects and Mechanisms," by Samioliova et al., Journal of Low Level Laser Therapy and Photobioactivation, Abstracts: Walt 1996, vol. 8, No. 1, Apr. 1996.

"Laser Irradiation on Blood Platelets," by Petrischey et al., Journal of Low Level Laser Therapy and Photobioactivation, Abstracts: Walt 1996, vol. 8, No. 1, Apr. 1996.

"Influence of Low Power Laser Radiation on Platelet Aggregation in Pathological Stress," by Kirichuk et al., Journal of Low Level Laser Therapy and Photobioactivation, Abstracts: Walt 1996, vol. 8, No. 1, Apr. 1996.

"Collagen and ventricular remodeling after acute myocardial infarction: concepts and hypotheses," by P. Whittaker, Steinkoff Verlag 1997.

"Role of Collagen in Acute Myocardial Infarct Expansion," by Whittaker et al., Circulation, vol. 84, No. 5, Nov. 1991, pp. 2123–2134.

Quickview Report, Piper Jaffray Research, CardioGenesis Corporation, Jun. 20, 1996, pp. 5 and 6.

The Effect of Laser Irradiation on the Release of bFGF from 3T3 Fibroblasts,: by Yu et al., Photochemistry and Photobioligy, vol. 59, No. 2, pp. 167–170, 1994 (Only p.167 Enclosed).

"Percutaneous Delivery of Low–Level Laser Energy Reverses Histamine–Induced Spasm in Atherosclerotic Yucatan Microswine," by Gal et al., Circulation, 1992; 86:756–768 (Only p. 756 Enclosed).

American Society for Laser Medicine and Surgery Abstracts, p. 9, containing Abstract Nos. 36, 38, 39 and 43, 1994.

Abstracts from the 68th Scientific Sessions, p. I–33, Circulation (Suppl.) 92:1995 (Page Contains Complete Abstracts 0151–0154), Nov. 1995.

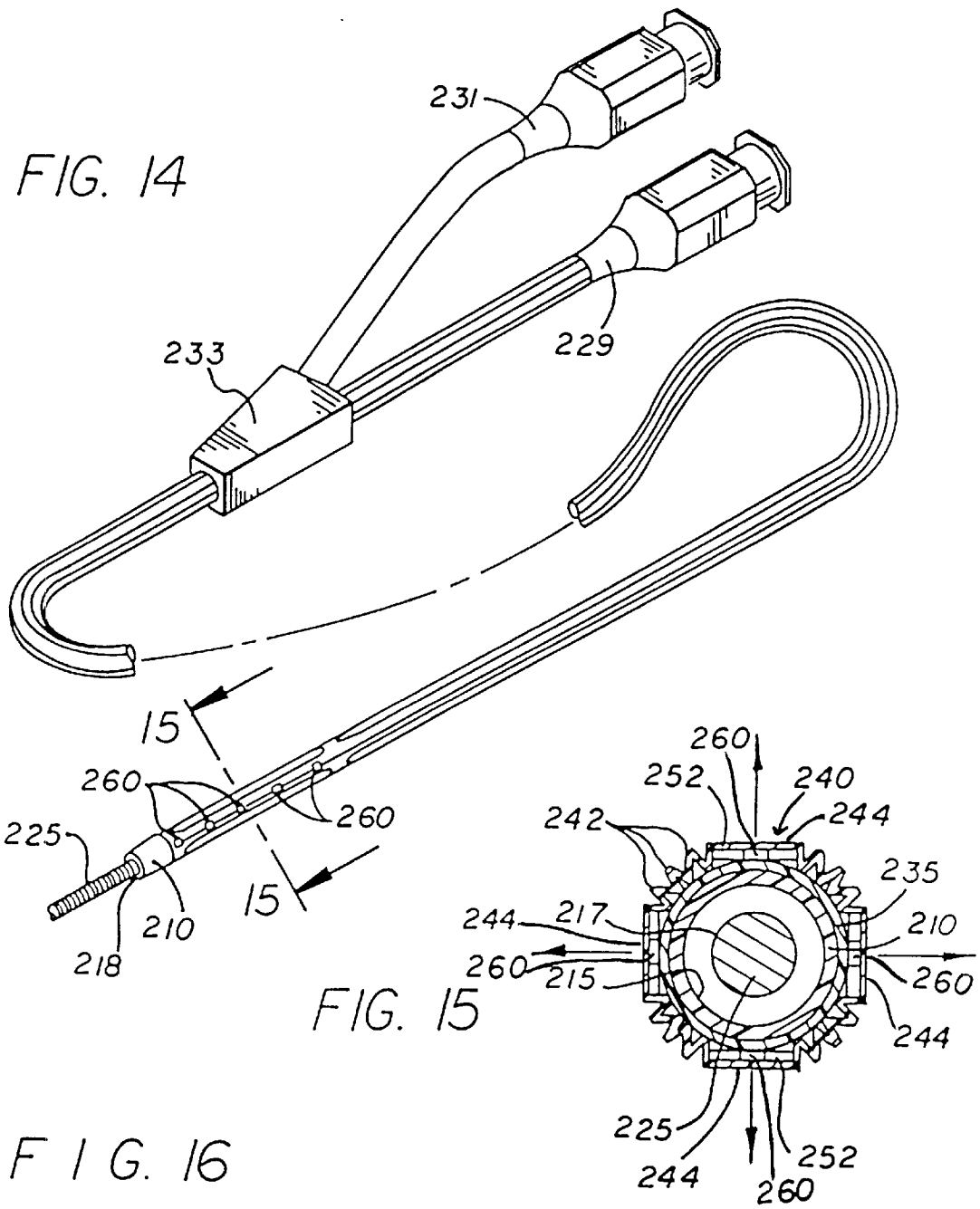
FIG. 14
FIG. 15
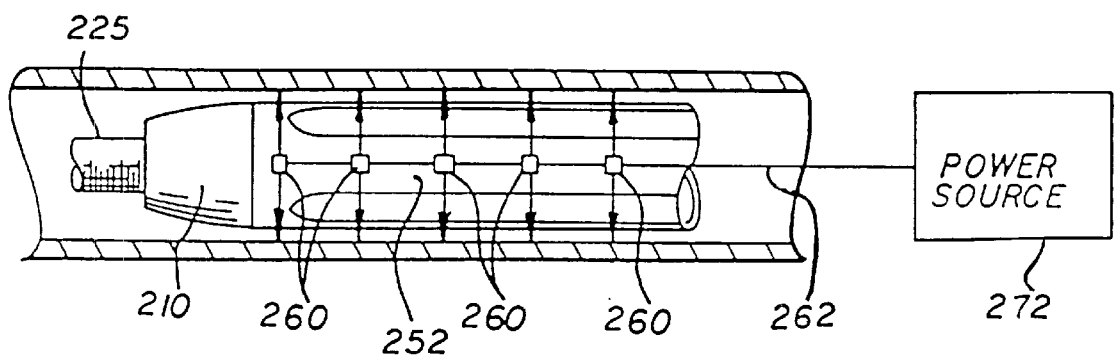
FIG. 16

METHOD AND APPARATUS FOR THERAPEUTIC LASER TREATMENT

RELATED APPLICATIONS

This application is a continuation-in-part of U.S. patent application Ser. No. 08/215,263, filed Mar. 21, 1994 now U.S. Pat. No. 5,616,140, and is also a continuation-in-part of U.S. patent application Ser. No. 08/703,488, filed Aug. 26, 1996 now U.S. Pat. No. 5,814,039.

BACKGROUND OF THE INVENTION

1. Field of the Invention

The present invention is directed to a method and apparatus for applying laser beam energy in the treatment of medical conditions. Specifically, the present invention is directed to a method and apparatus for applying low-level laser beam energy, using a vertical cavity surface-emitting laser or an array thereof, to promote angiogenesis of the heart muscle wall following cardiac ischemia, during and after myocardial revascularization, and immediately following acute myocardial infarction and for a time thereafter. Additionally, the present invention is directed to a method and apparatus for applying low power laser therapy directly to the coronary vasculature and blood system affected by these medical conditions.

2. Background

The number one killer in the U.S. and worldwide is heart disease accounting for 1,500,000 heart attacks in the U.S. and 500,000 U.S. deaths per year. As a result of coronary artery disease ("CAD"), individuals suffer from insufficient blood supply to the heart muscle. This can result in silent cardiac ischemia in which the patient is unaware that there is a deficiency of blood supply to the heart muscle. Another form of CAD manifests itself in chest pains—angina pectoris—and the disease in either of these forms can progress to myocardial infarct or acute complete deficiency of blood supply to the heart muscle.

When the disease progresses to this stage ("MI") there is pennanent damage to the heart muscle starting with deterioration of the heart muscle due to weakening of the collagen framework and progressing to expansion of the heart wall. If healing does not occur in time, the heart wall ruptures and death occurs.

The present methods of treatment involves drugs to thin the blood, drugs to reduce high blood pressure, balloon angioplasty and stents to expand the narrowed coronary arteries, thrombolytic drugs to open the blocked arteries in acute MI, and a number of invasive surgical procedures with their attendant mortality risks. After spending approximately $300 million on drug research in the past ten years no effective drug therapy has been discovered and the death rate from MI continues to remain at about 500,000/year in the U.S. and is bound to grow with the increase in the average age of the population.

The application of laser beam energy in the treatment of medical conditions such as wounds, ulcers, nerve injuries and muscle injuries is known. Studies have shown that low-power laser beam energy (1–500 mW) and in varying wavelengths (400–1300 nm) delivering 0.5–7 J/cm$^2$ is effective in the treatment of these various medical conditions.

Studies have shown that low power laser energy stimulates fibroblasts and other cells important in the wound healing process to release a number of growth factors in greater amounts than without laser photostimulation, thus enhancing and accelerating the wound healing process. Increased proliferation of fibroblasts and keratinocytes has been reported in a number of studies as well as the release of cytokines from Langerhans cells and the release of growth factors from macrophages.

Wei Yu reported in Photochemistry and Photobiology, 1994 that low energy laser irradiation increased the release of basic fibroblast growth factor (bfGF). bfGF is a potent mitogen and chemoattractant for fibroblasts and endothelial cells and induces a predominantly angiogenic response in the healing wound. These growth factors stimulate growth of new blood vessels in the healing wound ("angiogenesis"), increased collagen deposition, and increased tensile strength in the healing scar.

Of importance to this particular application, low power laser therapy has been shown to enhance and accelerate wound healing and reduce scar tissue while enhancing the collagen composition and tensile strength of the healed scar. Enwemeka reported this effect in healing rabbit tendons in Laser Therapy Journal—1994. A significant clinical demonstration of the increased tensile strength of scars healed with low power laser therapy was reported recently by Kleinman et al. in Laser Therapy Journal—1996.

The ability to influence and accelerate the formation of collagen and microcirculation immediately after MI by photomodulation is important in preventing the weakening of the collagen framework and subsequent expansion and rupture of the heart muscle which leads to death.

Low-level laser energy has also been known to have a profound effect on blood biochemical indexes, homeostasis, erythrocyte and leukocyte blood count, and platelet aggregation. In a study by Salansky published in The American Society of Laser Medicine and Surgery, transcutaneous application of 660 nm laser energy at 6 mW was shown to have a significant effect on leukocytes and erythrocytes. In that same study, photon irradiation resulted in significant activation of antioxidant enzymes, reduction of hypercoagulation, and increase of lipid peroxidation in stress-immobilized animals.

In the Laser Therapy Journal, Kipshidze published a study of 900 patients with acute MI whose intravenous blood was irradiated with low-power laser energy within the first four hours following MI. Data of organ-specific enzyme monitoring and ECG mapping showed limitation of the ischemic area. Moreover, antioxidant blood activity and blood and tissue oxygen contents increased. ECG monitoring showed that laser therapy had a high antiarrhythmic effect and reduced ventricular fibrillation. Intravenous laser irradiation was shown to significantly limit the ischemic damage and accelerate the scarring process.

Conventional low power laser therapeutic devices generally comprise a hand-held probe with a single laser beam source, or a large, stationary table console with attached probe(s) powered by a conventional fixed power supply. A common laser beam source is a laser diode. Laser diodes are commercially available in varying power and wavelength combinations. Large probes which contain multiple laser diodes affixed to a stand are also known. Such large, multi-beam devices are typically very expensive and require extensive involvement of medical personnel when treating a patient.

For example, in a device such as the large probe containing multiple beam sources discussed above, this device is typically affixed to a stand which has to be focused and controlled by a doctor or ancillary medical personnel. In addition to adding to the cost of the device and the treatment therewith, such a device requires a patient to travel to the location of the laser treatment device in order to obtain the laser therapy. Studies have shown that such treatment typically must be provided on a regular basis (e.g., every few hours or daily) once the treatment is initiated in order to be effective and to produce optimum results. This requires numerous patient visits to the treatment facility or extensive waiting on the part of the patient. As it is common for problems to arise which necessitate a patient missing a visit to the treatment facility, or for a patient to be inconsistent in the times at which appointments are scheduled, the efficiency of the treatment regimen may be lowered or the length of the treatment regimen (i.e., the number of patient visits) may be increased.

In the case of emergency medical conditions, such as MI, a conventional hand-held device is a less than optimal solution. More specifically, the operator of the device would be required to continuously apply the apply the laser energy when needed. This would result in added labor costs, thus making the device even more expensive. Further, self-application of laser energy is not feasible.

In addition to increasing the financial cost to the patient, a patient may be adversely affected by the number of required visits to the treatment facility in ways which are less tangible. That is, in addition to being away from family members, a patient is generally incapable of working or otherwise being productive while at the treatment facility. The high number of visits interferes with a patient's normal routine and can adversely affect a patient's job performance or home life.

Accordingly, a need exists for a method and apparatus for low-power laser treatment of MI, that is economical, convenient and more efficient than was previously possible.

SUMMARY OF THE INVENTION

The present invention overcomes the problems associated with prior art laser delivery devices by providing a method and apparatus for laser treatment of heart conditions. More specifically, the present invention solves the problems associated with the need for constant physician attention and inconsistent treatment delivery. The present invention also provides for a relatively low-cost, efficient, and portable method and apparatus for treating heart conditions as an adjunct to traditional methods for treating cardiac ischemia and MI treatment, and also as an adjunct to myocardial revascularization procedures.

The present invention achieves the above and other objectives through a preferred embodiment having a combination of laser beam energy from vertical cavity surface-emitting lasers ("VCSELs") employed in a treatment region near the heart. The present invention allows for the application of such treatments in a manner which does not require constant physician or ancillary medical personnel attention, once the device is activated, programmed and applied to the appropriate site.

The present invention provides a laser therapeutic device for applying laser treatment to the patient's heart in a systematic, pre-programmed manner to obtain optimum results while decreasing the cost associated with such treatment. The device includes a flexible bandage coupled to a power supply disposed on the bandage. An array of VCSELs are disposed in the flexible bandage and are operatively connected with the power supply. A controller is also connected to the power supply and the VCSELs and causes the VCSEL to fire for a predetermined period of time at specified intervals. A treatment regimen is stored by the controller. The flexible bandage is attached to the patient using a medical adhesive affixed to the laser-emitting side of the device. To provide a more sterile environment, a disposable clear microporous hydrophobic membrane sheet ("MHM") may be attached to the skin and the device adheres to this film. In operation, a physician may program a specific regimen in the device and allow the patient to wear the device attached to the body for an appropriate time period for healing, thus requiring less frequent visits for monitoring. As a result of the portability, design, and efficiency of application, laser therapy delivered by this method is more cost-effective than prior devices.

In another embodiment of the present invention, a bandage having two side sections is provided. Each side section is preferably half-moon shaped and surrounds an area of treatment on the patient's body. A series of VCSEL arrays are disposed within the bandage and are coupled to a controller/power supply, as described above. The VCSELs systematically provide low-level laser energy to a wide area proximate the patient's heart, vasculature, and blood system. The ends of each side bandage section may be connected to each other using a flexible polymer material.

In addition to the application of the laser beam energy from the bandage by direct application, the energy may be delivered to the heart through the use of optical fibers coupled to the laser bandage and temporarily implanted between the ribs of the patient using minimally invasive surgery. As with the previously discussed embodiments, a programmable source of laser beam energy coupled to the fibers permits the fibers to transmit the laser light along their length to a region of the heart.

In a fourth embodiment of the present invention, a disc is used to provide an implanted source of low-level laser energy directly to an area within the patient's body. The disc is attached to a power supply/controller, as described above. The power/supply controller is also coupled to a group of VCSEL arrays embedded in the disc. The VCSELs may be arranged circularly or in a parallel arrangement. The disc(s) is implanted by minimally invasive surgery into the appropriate area adjacent to the affected area and positioned to irradiate the designated area. Thus, low-level laser therapy may be effectively applied to the area to promote angiogenesis of the heart myocardium and healing of the heart myocardium.

A more complete understanding of the laser treatment method and apparatus will be afforded to those skilled in the art, as well as a realization of additional advantages and objects thereof, by a consideration of the following detailed description of the preferred embodiment. Reference will be made to the appended sheets of drawings which will first be described briefly.

BRIEF DESCRIPTION OF THE DRAWINGS

FIG. 14 is a perspective view of a sixth embodiment of a laser therapeutic apparatus of the present invention.

FIG. 15 is an end sectional view of the laser therapeutic apparatus as taken through the section 15—15 of FIG. 14.

FIG. 16 is a side sectional view of the laser therapeutic apparatus of FIG. 14.

DETAILED DESCRIPTION OF THE PREFERRED EMBODIMENT

Figure 1:
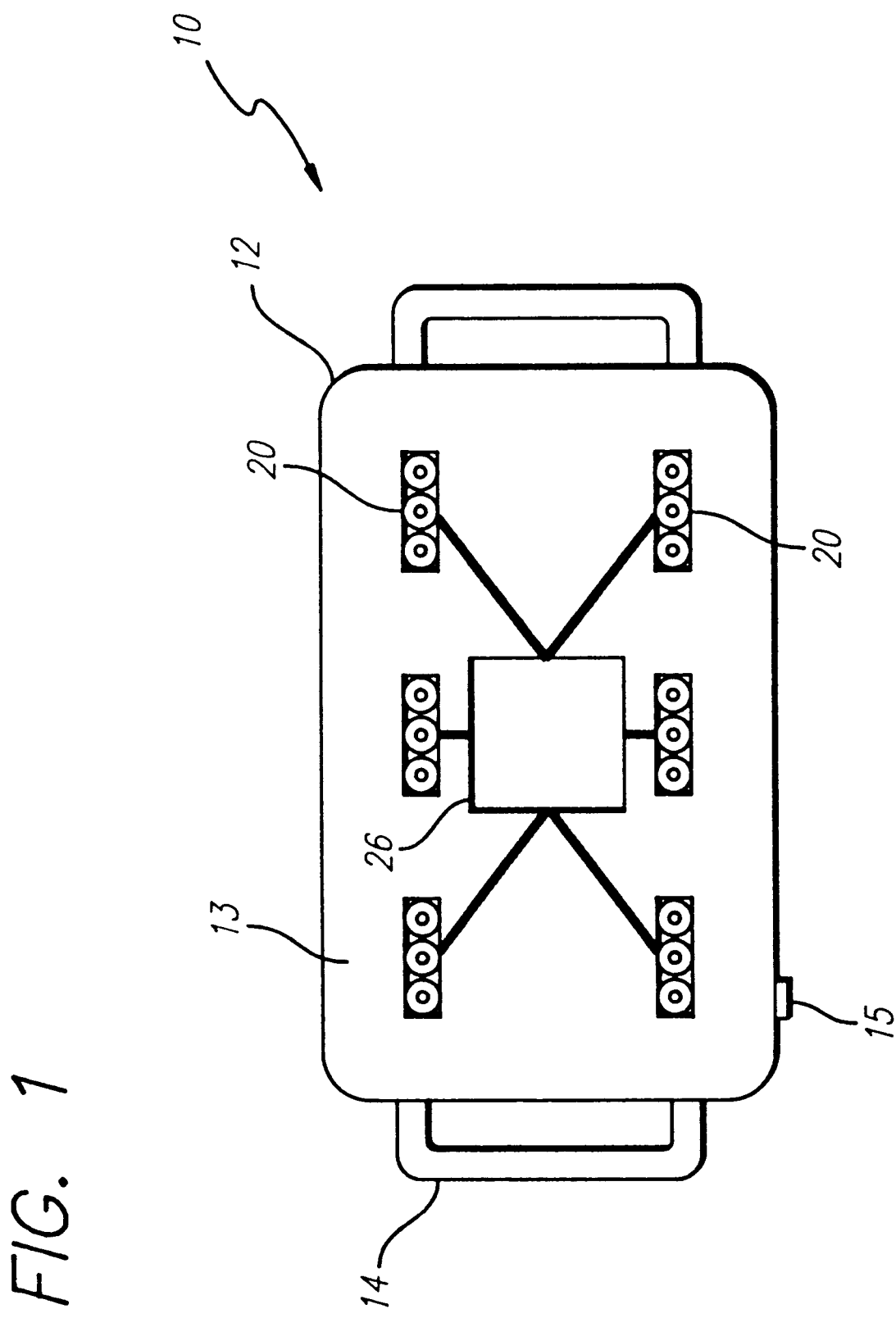
FIG. 1 is a top plan view of a first embodiment of a laser therapeutic apparatus in accordance with the present invention.
Figure 2:
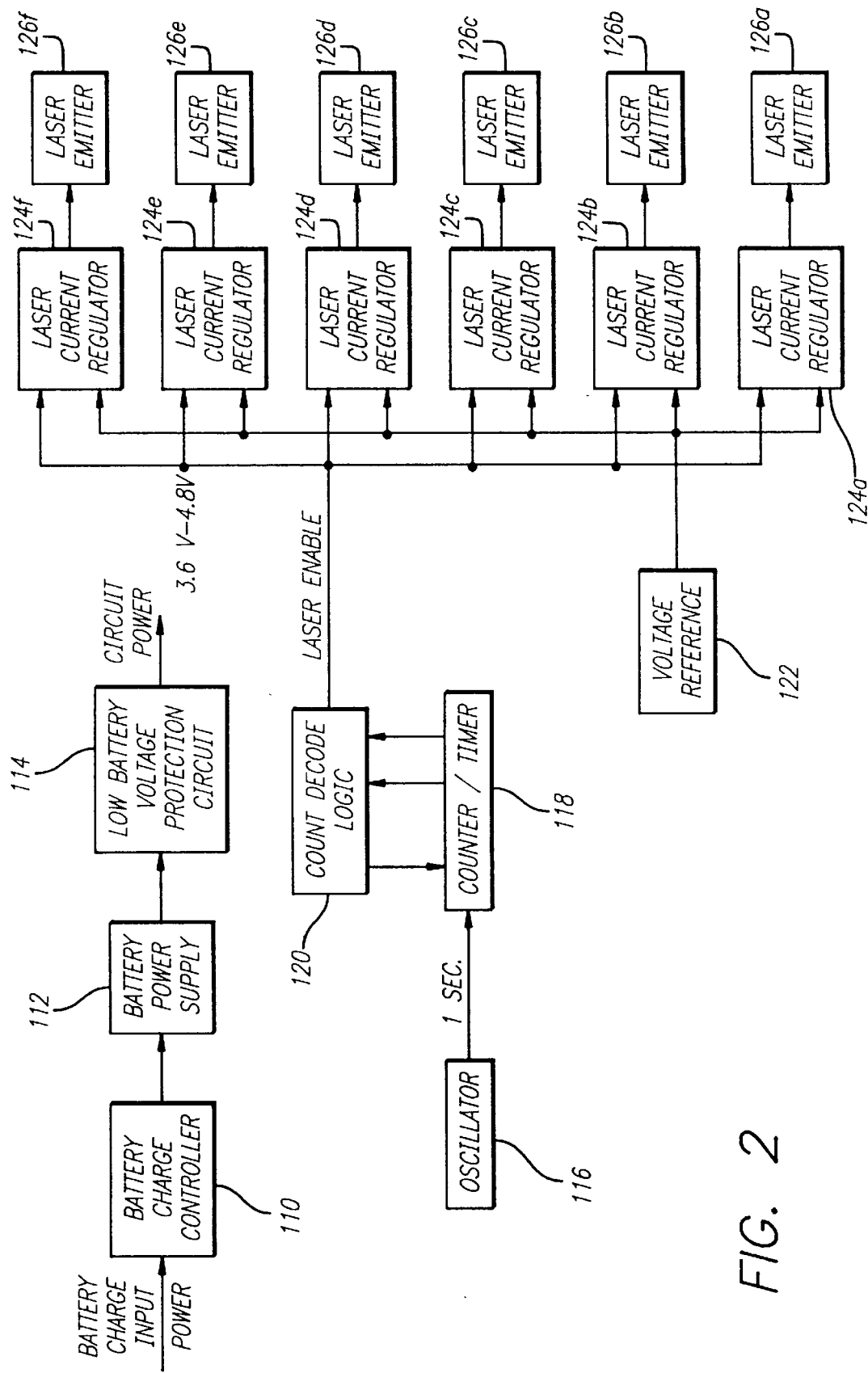
FIG. 2 is a block diagram showing a preferred embodiment of a power supply and control circuit for the laser therapeutic device of FIG. 1.
Figure 3:
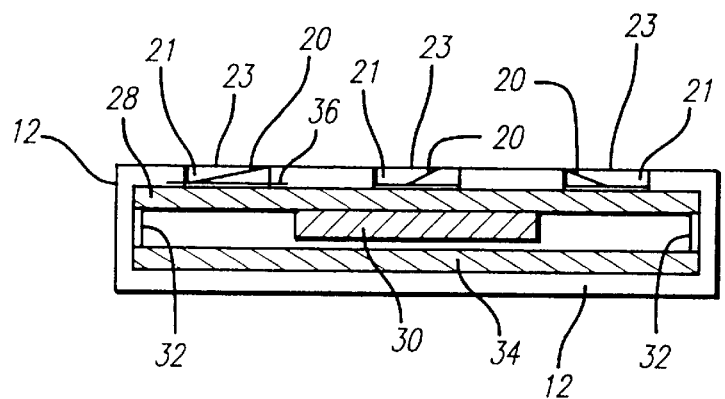
FIG. 3 is a cross-sectional side view of the laser therapeutic apparatus shown in FIG. 1.

FIGS. 1–3 illustrate a first preferred embodiment of the present invention. It should be understood that the following discussion of the presently preferred embodiments is not to be considered in a limiting sense. Rather, it is to be understood that numerous modifications, additions, and/or substitutions can be made to the preferred embodiments without departing from the spirit and scope of the present invention.

Referring to FIG. 1, a laser therapeutic device 10 in accordance with the first preferred embodiment includes a body or housing 12. In addition, an optically clear, breathable sterile polymer sheet may be affixed to the skin of the patient prior to attaching the device 10 to prevent contamination of the device or skin irritation. Preferably, an assortment of lasers 20 are distributed about an area of the surface 13 of the housing 12 and are interconnected by flexible, flat wire connectors 24. The flat wire connectors 24 lead to a central power supply and control circuit 26.

The "housing" 12 may actually be made of clear or optically clear biocompatible polymer material which is bonded to a flexible printed circuit board 28 and a flexible polymer battery. The circuit board may also be powered by an external power supply, such as a transformer, for converting AC voltages into DC voltages. The power supply, in turn, is connected to a conventional household AC current. The structure will be discussed in greater detail below.

The lasers 20 are preferably vertical-cavity surface-emitting lasers ("VCSELs") having a nominal power output of 2.6 mW and a wavelength on the order of 400–1300 nanometers, with the preferred wavelength being approximately 780 nanometers. The preferred power output of the lasers is at least 5–10 mW per VCSEL chip.

VCSELs are known and comprise semiconductor lasers which emit a beam normal to the surface of the semiconductor substrate. The semiconductor includes aluminum arsenide (AlAs) or gallium arsenide (GaAs), or a combination thereof. Each VCSEL has a self-contained, high-reflectivity mirror structure forming a cavity to produce the beam. Additional lenses may be used to focus or defocus the beam. In addition, polarizing birefringent material may be placed over the VCSEL to modify the polarization of the beam, as required. A typical VCSEL may be on the order of 300 micrometers long, have an operational power threshold below 1 milliamp, and consume very little power compared with conventional laser diodes (which may also be used in the present invention), thus enabling numerous VCSELs to be powered from a single battery source. For purposes of the discussion below, it should be clear that where the terms "laser" or "lasers" are used, the preferred embodiment uses VCSELs, but conventional laser diodes are also applicable.

In the present invention, the VCSELs are preferably 400 micrometers in height or less and surface-mounted on a chip of silicon, copper, or ceramic. The entire VCSEL chip is encased in clear epoxy following mounting, resulting in a low-profile laser device. A single VCSEL 20 may be mounted on a chip or a VCSEL array may be used, each chip having two or four VCSELs. Each chip array has its own wavelength, although a group of wavelengths may be used, with each wavelength ranging from 400–1300 nm. The VCSEL chips are then distributed on the flexible polymer circuit material in accordance with the design of the device and interconnected using flexible electrical connectors or by printed conductive ink interconnects. The flexible polymer battery is then surface-mounted on a reverse side of the flexible circuit material. The entire device may then be sealed in a biocompatible flexible polymer 0.5 mm in thickness, thereby resulting in a flexible sheet or bandage with a total thickness of approximately 4 mm.

The programmable power supply and control circuit 26, the operation of which may be initiated by means of a single-pole, double-throw, or pressure switch 15, provides power and timing control for operation of the lasers. The timing control includes initiating the operation of the lasers for a predetermined time period in accordance with a prescribed laser treatment regimen. A control device for performing such a function is known in the art and may comprise a programmable controller having a 24 hour timing function and which initiates operation of the laser diode for a predetermined period of time over the course of a 24-hour period. Preferably, the therapeutic device of the present invention is programmed to deliver two-minutes of laser therapy at four-hour intervals for five to six days. To prevent the device from being accidentally deprogrammed during the critical healing period, the switch 16 may be an "on only" switch that cannot be turned off by the patient. Alternatively, the device 10 may include a standard on/off switch that does not initiate programming of the device 10, but rather initiates laser firing immediately. Such a switch would permit use of the device by the patient in the absence of medical personnel.

A preferred embodiment of a controller/power supply circuit 26 is shown in FIG. 2. A battery charge controller 10, which may be connected to an external power source, supplies a battery power supply 112 with a charge when the charge controller 110 is connected to the external source. When an optimum charge level is reached, the charge controller ceases supplying the battery 112 with the charge. Preferably, the battery 112 is capable of maintaining a charge sufficient for one week of laser therapy, based on a treatment being provided for two minutes every four hours or a duty cycle of less than 5%. A low battery voltage protection circuit 114 regulates the power supplied by the battery 112 and provide a voltage output between 3.6 and 4.8 volts. The protection circuit 114 ceases the supply of power if the voltage drops below the threshold level of 3.6 volts to avoid damage to circuit components. The power supplied by the protection circuit 114 is used to power the circuit components as well as the lasers. An oscillator 116 is provided which supplies pulses at one second intervals to a counter/timer circuit 118. The counter/timer circuit 118 simply counts the pulses while a count decode logic circuit 120 monitors the count.

The count decode logic circuit 120 is a multipurpose logic circuit which may comprise, for example, a PAL (programmable array logic) or a PLA (programmable logic array) that may be programmed to detect certain counts, e.g., 14,400 which would correspond to four hours of time and 120 which would correspond to two minutes of time. The count decode logic circuit 120 would be capable of maintaining the stored timing program (and, therefore, the prescribed regimen) without power being applied thereto. The count decode logic circuit 120 may also comprise a discrete logic circuit formed of standard logic components. While such a circuit would be more cost effective from a low-volume manufacturing perspective, the preferred count decode logic circuit 120 comprises a programmable logic circuit to afford maximum flexibility in operation of the laser therapeutic device of the present invention.

Upon detecting the programmed count, the count decode logic circuit 120 outputs a laser enable pulse which enables laser current regulator circuits 124 which regulate the power to each laser diode 20. The regulator circuits 124, which are known in the art and which compare the current with a known voltage reference in order to maintain a constant current output, receive a voltage reference input from a voltage reference circuit 122. The voltage reference circuit 122 may comprise an active bandgap zener diode which supplies a constant voltage output (on the order of 1.2 to 1.5 volts) regardless of the voltage of the battery 112. At the same time, the count decode logic circuit 120 provides a RESET pulse to the counter/timer circuit 118 to reset the count, and the counter/timer circuit 118 continues counting the pulses from the oscillator 116.

The laser enable pulse remains active for the programmed length of treatment, e.g., two minutes, or 120 counts of the counter/timer circuit 118. While enabled, the current regulators 124 in the lasers 20 use the input from the voltage reference circuit 122 to provide a predetermined amount of current to produce a beam having, for example, 2.6 milliwatts. The beams are produced by the laser emitters 126. The logic circuit 120 continues to monitor the count in the counter 118 and detects when the count reaches a programmed amount corresponding to the prescribed treatment length (e.g., 120), and then terminates the laser enable pulse. At the same time, the logic circuit 120 provides a RESET pulse to reset the count in the counter/timer circuit 118, and the cycle begins again.

To preserve battery power, the count decode logic circuit 120 may be programmed to provide a pulse to individual regulator circuits 122. This configuration permits sequential firing of the VCSEL arrays rather than simultaneous firing of all VCSEL arrays. Thus, particular areas of the patient's heart may be pinpointed for laser treatment. Alternatively, multiple laser enable pulses may be provided.

In operation, the laser therapeutic device 10 may be used to promote angiogenesis of the heart myocardium following myocardial infarction, cardiac ischemia, or other cardiac events. The device 10 may also be used as an adjunct to myocardial revascularization procedures, such as by-pass procedures and minimally invasive by-pass procedures. The device 10 is affixed to the chest of a patient by a physician or ancillary medical personnel such that the housing 12, with sterile, disposable clear biocompatible polymer cover 38 or MHM sheet in place, is positioned over the chest, side, or back of the patient, with the lasers 20 being focused between the patient's ribs through the intercostal cartilage to reach the appropriate area of the heart. The device may also be placed proximate a major artery, such as the carotid, brachial, or femoral to supply laser energy to the blood system. Alternatively, a sterile clear, birefringent polarizing sheet could be attached via medical adhesive to the patient's skin and the device attached thereto by a medical adhesive.

The controller/power supply circuit 26 is installed on a single flexible circuit board 28 which may be sufficiently thin (e.g., on the order of one millimeter) to be encapsulated by a polymer sheet so as to be formed integral therewith. The controller/power supply circuit 26 illustrated in FIG. 2 may be made of multiple circuit components which are readily available from electronics suppliers or may be implemented in an application specific integrated circuit (ASIC) to reduce the size and complexity thereof.

Referring now to FIG. 3, the partial cross-sectional side view of the laser therapeutic device 10 shown in FIG. 1 reveals a flexible printed circuit board 28 that supports the lasers 20 and is enclosed within a flexible polymer case 12. The flexible printed circuit boards may be made of a polyester material and the electrical interconnects and circuit design are printed with flexible, electrically conductive ink, such as developed by Polyflex Circuits Corporation. Flexible circuits may also be made using ULTEM (a trademark of General Electric Corp.) or Kapton (a trademark of Dupont Corp.). The housing 12 is provided with openings 21 formed therein to accommodate the light produced by lasers 20. The openings 21 may be provided with clear windows or clear biocompatible polymer over the clear epoxy laser chip encapsulant. The clear windows 23 are preferably formed of optically clear biocompatible polymer which is part of the housing 12. However, the windows may also be formed of glass, plastic, or other suitable materials.

The controller/power supply circuit 26 preferably includes a three volt, wafer thin, flexible, polymer battery 34 and a programmable controller 30. Alternatively, the battery 34 could be a simple three volt lithium battery or a rechargeable nickel-metal hydride battery. Preferably, the battery can provide sufficient power for a seven day treatment regimen. In the case of the nickel-metal hydride battery, these batteries could be recharged after a five or six day treatment cycle using known methods. Alternatively, a transformer or other appropriate power supply may be used. A power supply would transform household AC voltages to DC voltages for use by the device.

A pre-formed, sterilized, disposable resilient cover (not shown) may be used to encase the device 10. The cover has a plurality of openings formed therein to accommodate the laser beams produced by the lasers. The cover 38, which is preferably formed of the same biocompatible polymer as used in the housing 12, is held in place by a friction fit over the housing 12. With the cover in place, the entire structure of the device has a thickness of approximately four millimeters. The cover 38 further serves as a sterile surface between the device 10 and the patient's body. As discussed above, an optically clear, sterilizable sheet (not shown) may be placed on the patient's chest using a medical adhesive. The sheet 39 prevents bacteria from contacting either the patient or the device 10. Each sheet 39 is disposable and a new sheet 39 should be provided for separate treatments.

The operation of the therapeutic device 10 is initiated by the switch 15. Preferably, in use the switch 15 is covered by the biocompatible polymer cover 38 so that the patient will not inadvertently turn the device off. The doctor or ancillary medical personnel operates the switch 15 prior to installing the sterilized polymer cover 38 about the housing 12. After the switch 15 is operated, the device 10 is applied to the patient's chest or other appropriate area and the laser therapy begins. In operation, the laser energy from the device 10 irradiates the appropriate treatment area of the heart myocardium. Specifically, the VCSEL arrays 20 are repetitively fired at the appropriate wavelength and power so as to penetrate the patient's body and reach the myocardium or other appropriate vasculature system of the heart. Wavelengths of 40 to 1300 nanometers may be selected, although a wavelength of 780 nm is preferred.

The programmable controller 30, is preferably a low-power consumption device which, as discussed, is capable of approximately one week of operation from a single battery charge. Therapeutic devices 10 having different treatment regimens programmed therein could be provided, with the physician selecting a particular device in accordance with an appropriate regimen depending on the patient's condition. Alternatively, the controller 30 may be provided with a PCMCIA port which interfaces with a so-called "smart card" or master programming card which can be inserted therein and a treatment regimen may be downloaded to the controller 30 by the treating physician. Sensors to monitor heart and body functions may be included in the device design and information regarding these functions may be relayed to a central nurses' station for monitoring the patient's status.

In a preferred embodiment of the present invention, a time period can be provided between the operation of the switch 15 and the actual initiation of the laser treatment regimen to allow sufficient time for the therapeutic device 10 to be properly positioned on the patient's body prior to initiation of the laser therapy. In an alternative embodiment, the switch 15 could be a pressure switch which is activated by the placement of the polymer cover 38 on the housing 12. By placing the polymer casing about the housing 12, the pressure switch 15 would be activated, thereby initiating the laser treatment regimen.

After being located on the patient's body, the patient simply wears the therapeutic device 10 for the prescribed period of time. The therapeutic device automatically delivers the prescribed laser therapy as determined by the programmable controller 30. In this fashion, the attending physician or other medical personnel places the therapeutic device 10 either on the appropriate area of the patient's body or implants the device adjacent to the area of interest using minimally invasive surgery. The time-consuming, costly, and ill-timed applications of the prior art laser treatment regimens are replaced by an efficient, programmed laser treatment regimen over the course of a week. On an emergency basis, the attending personnel may be performing other time-critical tasks while the laser therapy is being administered. Due to the small size and low cost of the device, emergency vehicles and emergency rooms may maintain a supply of such devices to utilize the potential life-saving effects of the treatment. As a result, many lives can be saved.

A clear advantage of treatment using the laser therapeutic device 10, is the freedom provided to the patient. For example, depending upon the nature of the prescribed laser therapy, the patient may only need to wear the therapeutic device 10 during certain hours of the day (e.g., while sleeping). In order to ensure that the patient properly positions the therapeutic device 10 on the body, the physician could outline the proper location on the body with a waterproof marking pen. The patient will not be permanently marked using such a pen, since the body will naturally eliminate the marks over the course of one to two weeks. In the interim, the patient will be provided with a clearly visible indicator as to the appropriate location of the therapeutic device 10 on the body, enabling the patient to remove the device 10 for purposes of bathing, etc.

Figure 4:
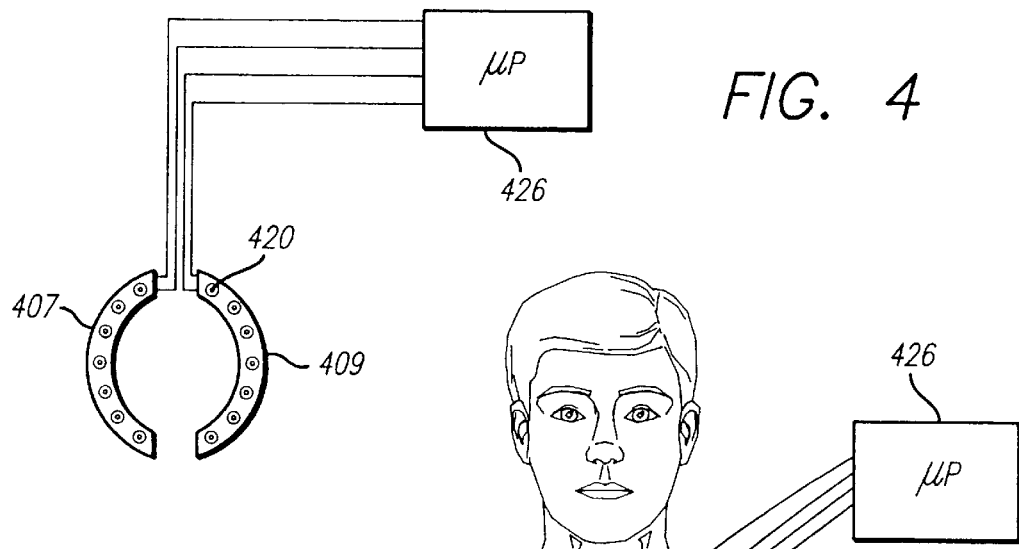
FIG. 4 is a plan view of a second embodiment of a laser therapeutic apparatus in accordance with the present invention.
Figure 5:
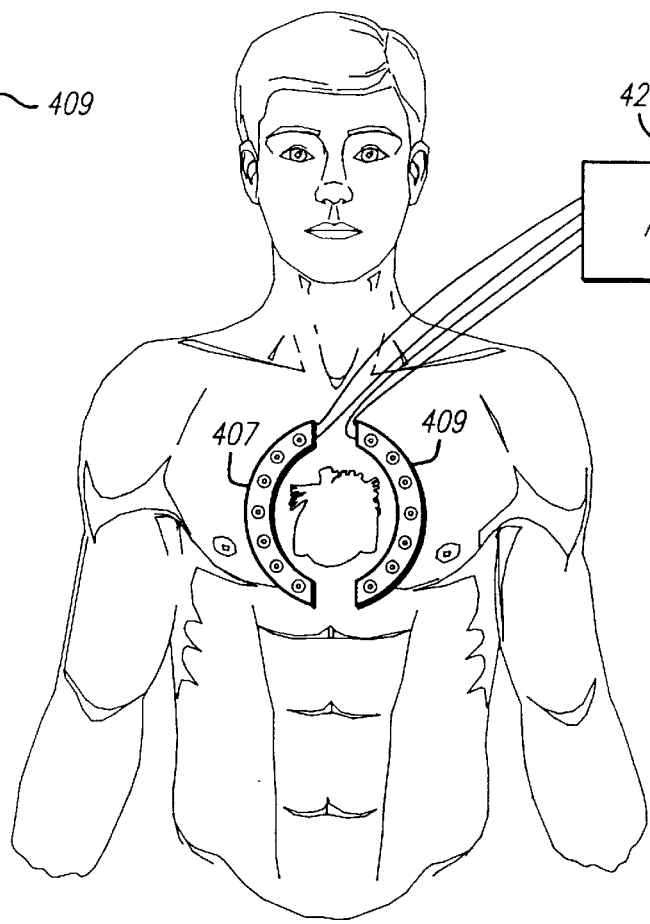
FIG. 5 is a plan view of the second embodiment of the apparatus of the present invention as attached to a patient.
Figure 6:
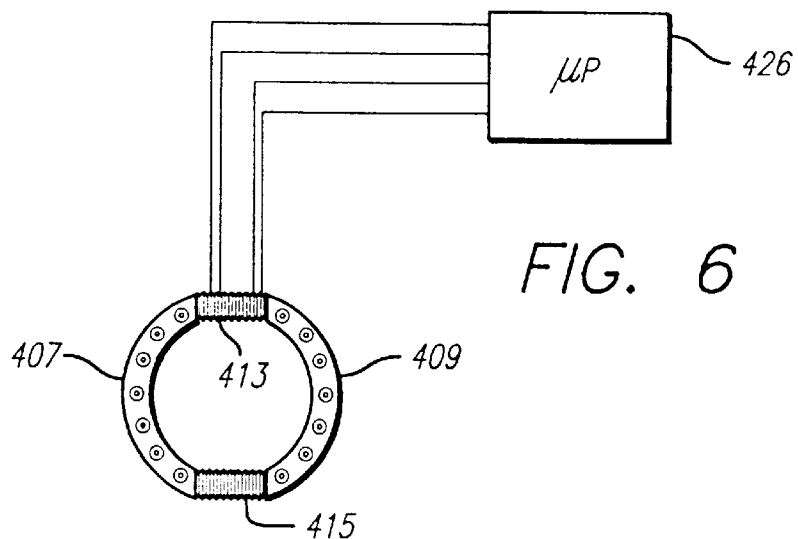
FIG. 6 is a plan view of a modified version of the second embodiment of the apparatus of the present invention.

FIGS. 4–6 illustrate a second preferred embodiment of the laser therapeutic device 40 in accordance with the present invention. The embodiment shown in FIG. 4 is also suitable for use in treatment of MI and cardiac ischemia, but may be used to treat ulcers or open wounds located on a patient's body. The device 40 includes two side bandage sections, a first semi-circular or half-moon bandage section 407 and a second semi-circular or half-moon bandage section 409. Flexible polyester circuit material carries three VCSEL chips 420 connected in series by electrically conductive ink interconnects and are sandwiched between an optically clear biocompatible polymer allowing transmission of the laser beam. The control circuit and power supply are mounted on flexible polyester material as in the preferred embodiment discussed above. The split bandage 407, 409 is attached by medical adhesive to a sterile, disposable optically clear sheet which is attached to the patient's skin. The control circuit/power supply may be worn on the patient's arm or other strategic location of the body. The device may also have an LED mounted on the control circuit/power supply, as discussed above, to indicate the operational status of the device as well as the battery status. The power supply may be affixed to another area of the patient or carried by the patient in a portable fashion. As discussed above, the sterile, optically clear disposable sheet may be a microporous hydrophobic membrane material as known in the art and used to prevent bacterial contamination of the skin, wound, and device. Alternatively, a sterile disposable clear polarizing birefringent sheet may be attached to the skin and the semicircular sections 407, 409 attached to the sheet using a known medical adhesive.

As shown in FIG. 5, the device 40 is affixed to the chest of a patient using a medical adhesive. An optically clear, sterile sheet may also be placed between the device and the patient's body to prevent bacterial contamination. The two sections 407, 409 may be spaced farther apart to cover a larger area of the patient's chest. The laser energy from the VCSEL arrays can then penetrate the patient's chest and "surround" a particular area. The device may also be used to cover two distinct areas of the patient's chest. FIG. 6 shows an alternative structure for the device 40, wherein expandable polymer sections 413, 415 connects the respective ends of the two side sections 407, 409.

Figure 7:
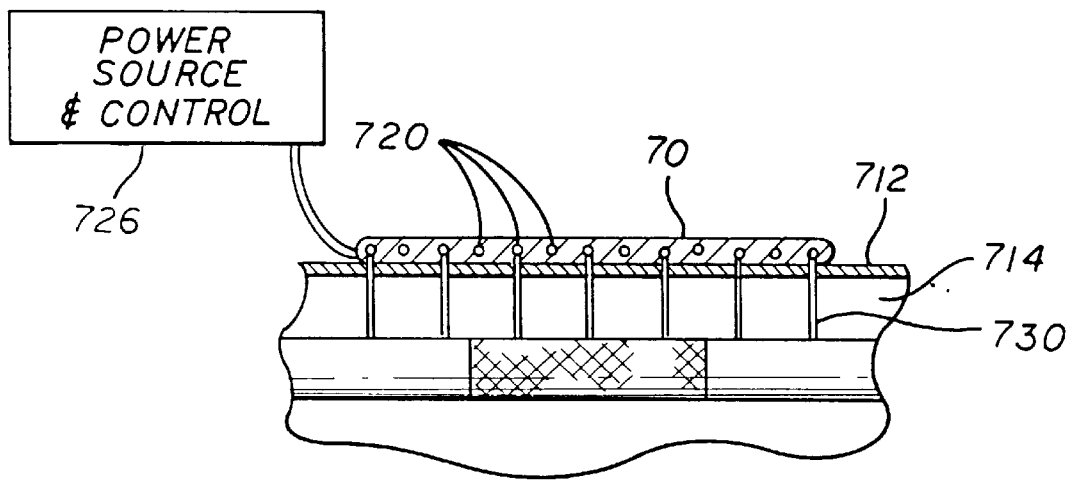
FIG. 7 is a side view of a third embodiment of a laser therapeutic apparatus in accordance with the present invention.

FIG. 7 illustrates a third preferred embodiment of the laser treatment device of the present invention, that delivers laser beam energy directly to deeper body structures, including heart vasculature when the targeted area is beyond the reach of the devices discussed above. Using interstitial low level laser therapy ("ILLLT") or percutaneous low-level laser therapy ("PLLLT"), the required energy can reach the desired area at the required depth to thereby produce biostimulative healing of the affected area. The embodiment is similar to the first embodiment with the lasers 720 being coupled to fiber optic strands or waveguides 730. The strands or waveguides 730 are coupled to the VCSELs 720 using a plate (not shown) having a thickness of approximately 100 micrometers. The plate is affixed to the VCSEL using optical epoxy and embedded in the polymer housing 12 (see FIG. 1). Alternatively, the plate may be embedded in the cover 38 (see FIG. 1) discussed above. The strands or waveguides 730 extend through the patient's dermal layers 712, 714 and related tissues to conduct the laser beam energy to the targeted area. The optical fibers and waveguides may be fitted with various lenses to focus or defocus the beam, including side firing lenses to further direct and guide the laser beam energy as required. The controller/power supply circuit 726 is similar to the controller/power supply discussed above with respect to the first embodiment.

The narrow, circular beam characteristic of VCSELs allows for high coupling efficiency to fibers. Thus, the optical fibers 780 may be as small as a typical surgical suture or as in the case of a waveguide, as small as one millimeter or less in diameter. The optical fibers or waveguides may be implanted along the location of a surgical incision or the optical fibers or waveguides may be percutaneously implanted by an eighteen gauge needle implanting device using ultrasound and MRI guidance to the desired location requiring laser therapy. By providing this minimally invasive method of laser therapy delivery, the fibers 780 may be directed between the ribs of the patient and through the intercostal cartilage to the targeted area of MI, cardiac ischemia, or area undergoing transmyocardial revascularization. Or in the case of coronary by-pass procedures, the optical fibers 780 would be implanted at the time of surgery to allow PLLLT for the required healing period. Thus, low power laser therapy may be delivered anywhere in the patient's body and can remain in place until the required laser therapy treatment has completed. Once the therapy is completed, the optical fibers 780 may be removed from the patient much like a suture. As with the other embodiments described above, this embodiment is not limited to applications in the cardiovascular field, but may be applied to vascular grafts, organ transplants, internal vasculature, deep wounds, heart, liver, kidney, pancreas, or any deep body cavity or organ.

Figure 8:
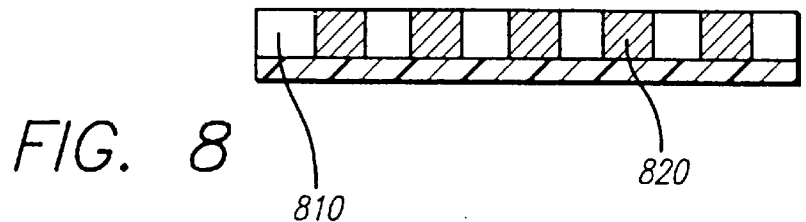
FIG. 8 is a cross-sectional view of the laser therapeutic apparatus shown in FIG. 7.
Figure 9:
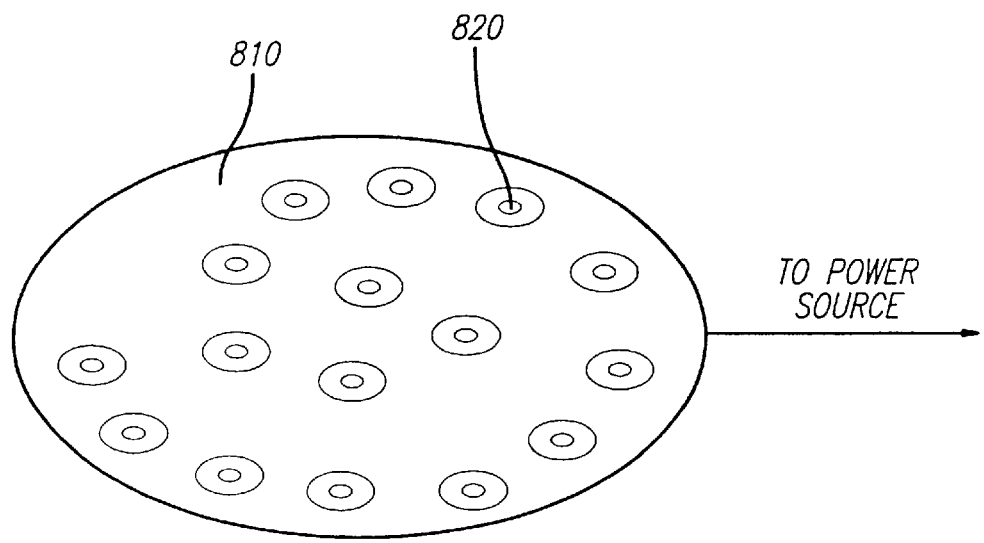
FIG. 9 is a plan view of a fourth embodiment of a laser therapeutic apparatus of the present invention.
Figure 10:
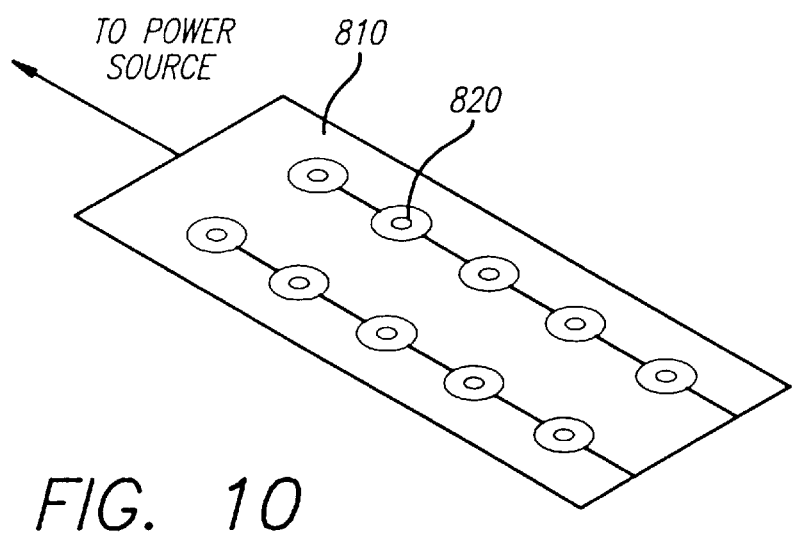
FIG. 10 is a plan view of a modified version of the fourth embodiment of the laser therapeutic apparatus of the present invention.

FIGS. 8–10 show a fourth preferred embodiment of the laser treatment device of the present invention. In this preferred embodiment, low level laser energy is delivered to the heart through an implantable disc 810 or strip of VCSELs. The disc is formed of flexible, polymer circuit material and has a diameter between 18 and 30 millimeters. The disc 810 has a preferred thickness of less than 400 micrometers and is sealed in an optically clear hydrophobic implantable grade biocompatible polymer. Alternatively, the entire device may be coated with a microscopic coating of optically clear polymer. A number of individual VCSEL or VCSEL arrays 820 are mounted onto the device. The VCSEL arrays 820 are arranged at intervals on the disc 810 to distribute laser energy over the affected area. Preferably, the device includes four VCSEL arrays, each array including two VCSELs. Also, a strip of VCSELs may be arranged in a parallel arrangement as shown in FIG. 10. Each VCSEL array has an operating power of 4–8 mW.

During operation, the disc 810 may be programmed to operate in either a pulsed mode or a continuous wave ("CW") mode. In the pulsed mode, the VCSEL may operate at one watt for a nanosecond, the total photon density and average power being less than in the CW mode. The disc 810 may be programmed to fire each VCSEL array 820 in sequence. Specifically, the first VCSEL array would emit laser energy for a period of five seconds, for example. Following this period, a second VCSEL array would emit energy for a period of five seconds, etc.

Figure 11:
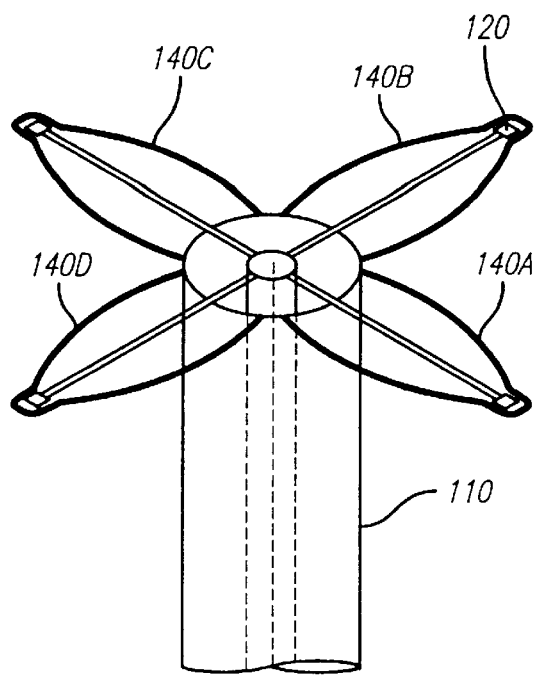
FIG. 11 is a perspective view of a fifth embodiment of a laser therapeutic apparatus of the present invention.
Figure 12:
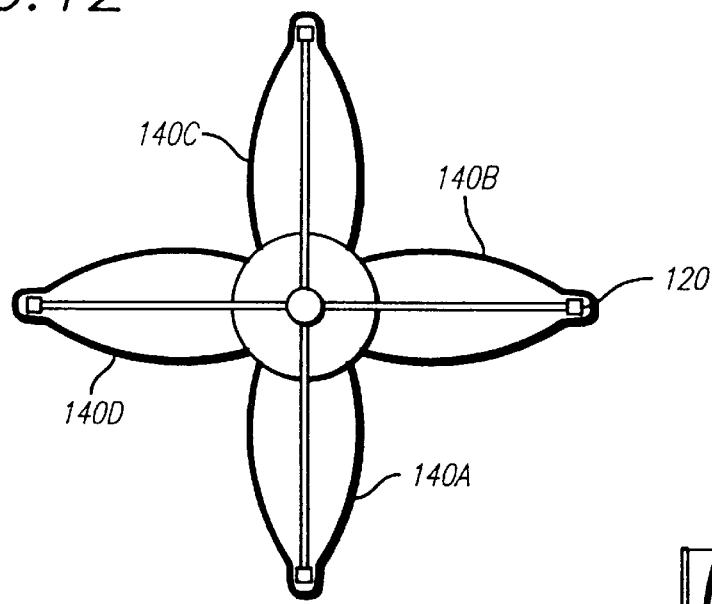
FIG. 12 is a top view of the laser therapeutic apparatus of FIG. 11.
Figure 13:
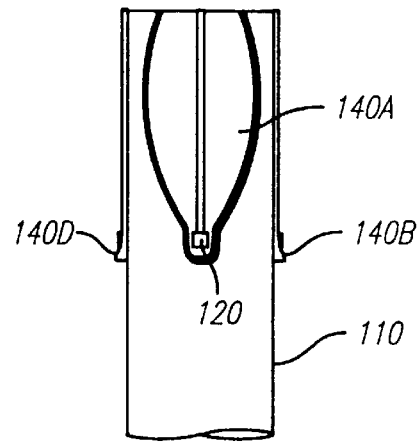
FIG. 13 is a side view of the laser therapeutic apparatus of FIG. 11.

FIGS. 11–13 show a fifth embodiment of the laser treatment device of the present invention. The device 110 has an "umbrella" shape and features a hollow, cylindrical shaft 140 having an electrical lead 160 coupled to a controller/power supply (not shown). The controller/power supply is similar to the controller/power supply described above with respect to the previous embodiments. A series of frames 180 are coupled to an end of the shaft 140, with frames overlapping each other proximate the shaft end. The frames 180 may be comprised of a high strength, surgically sterile material, such as Nitinol. The frames 180 surround an electrically conductive, flexible material, such as polyester, that gradually extends from the shaft 140 to a wide point before tapering at an outer end. For each frame, a VCSEL 120 is mounted on the outer end of the flexible material. The VCSEL 120 is operatively connected to an electrical interconnect 145 that runs along the length of each frame. Each interconnect 145 is connected to the electrical lead 160, thus providing power and programmable control to the VCSEL 120. Optionally, fiber optic strands may be employed to deliver laser treatment. As discussed above, the strands would terminate at a coupling plate that is optically coupled to a VCSEL 120.

Each frame 180 is initially in an unexpanded position as shown in FIG. 13. In the unexpanded state, the frame 180 lies along an outer surface of the shaft 140. A physician may deploy the device manually as shown in FIGS. 11 and 12. Once manually deployed, a physician may endoscopically insert the device 110 into a treatment area using a trocar or similar guide. Alternatively, the device 110 may be inserted percutaneously using minimally invasive surgery. A physician may then guide the device 110 to a targeted area using ultrasonic imaging and/or MRI.

FIGS. 14–16 show a sixth embodiment of the laser treatment apparatus of the present invention. The device 220 includes a catheter 212 having a housing 210 extending from a proximal end (not shown) to a distal end 218. The housing 210 is generally cylindrical and is comprised of flexible plastic or a similarly resiliently flexible material. The distal end 218 of the housing 210 is made in accordance with a dual lumen design. The space between the inner wall 215 of the housing and the outer edge 217 of the guidewire 225 defines a dual guidewire/inflation lumen 230 having a guidewire 225 therein. The dual lumen 230 is generally annular in cross section. The guidewire 225 is comprised of stainless steel or platinum or an equivalent thereof.

As shown in FIG. 14, the catheter 212 includes a tube 229 that provides inflation fluid to the balloon 235. Inflation fluid is evacuated through tube 231. The inflation tube 229 and evacuation tube 231 combine at junction box 233 to communicate with the dual lumen 230. The dual lumen 230 communicates with the interior of a balloon 235 located near the distal end 218 of the catheter. The balloon 235 typically is formed from an inelastic material to permit uniform inflation to a predetermined volume. The balloon 235, when inflated with inflation fluid fed from an inflation tube 229 that communicates with the dual lumen 230, expands to apply therapeutic outward pressure against the interior walls of an occluded blood vessel in which the balloon 235 is positioned. Inflation fluid is removed utilizing an evacution table 231 that communicates with the dual lumen 230.

As shown in detail in FIG. 15, a flexible sleeve 240 surrounds the balloon 235 near the distal end 218 of the catheter. The sleeve 240 has a thickness of approximately 0.25–0.50 mm and is preferably formed of optically transparent soft silicone or a similar material. The sleeve 240 is molded to accommodate balloon catheters of different sizes. When the balloon 235 is not inflated, the sleeve 240 fits tightly over the balloon 235. The sleeve 240 contains flat portions 244 along the top, bottom, and sides of the balloon to accommodate conductive strips 252 embedded therein. To accommodate the expansion of the balloon 235, the sleeve 240 contains pleats 242. When the balloon 235 is in its expanded state, the pleats 242 expand to permit the flat portions 244 of the sleeve 240 to maintain the same orientation with respect to the balloon 235 as in the uninflated state. The transparent soft silicone material permits the transfer of laser energy therethrough, as described below.

Four electrically conductive flexible film strips 252 are embedded into the flat rectangular portions of the sleeve 235 adjacent to the balloon 240. Each electrically conductive film strip 252 has a thickness of approximately 0.003 inches. The film strips 252 are aligned longitudinally along the outer circumference of the balloon 235. Accordingly, the length of each film strip is approximately the same length as the balloon 235. This length will vary depending upon the length of the balloon. Each film strip 252 is preferably formed of a polyester conductive material, such as Kapton or Ultem. In the uninflated state, the conductive film strips are aligned along the top, bottom, and sides of the balloon in the flat portions 244 of the sleeve 240. When the balloon 235 is filled with inflation fluid via the distal inflation lumen 230, the flexible nature of the sleeve allows the conductive film strips 252 to maintain this orientation. Each film strip 252 is electrically conductive and includes electrical interconnections etched along the surface. The various interconnections permit the surface-mounting of various electrical devices on the film strip 252. Several VCSEL chips 260 are surface-mounted onto each film strip 252.

FIG. 16 depicts a catheter having a plurality of VCSEL chips 260 disposed on conductive film strip 252, without the use of a sleeve or balloon. Each strip 252 contains 4–8 VCSEL chips spaced 3 millimeters apart and connected to an external power source 272 via a lead 262. The chips of VCSELs are interconnected with flexible electrical connectors etched on the strip 252, or printed on the strip 252 using conducting ink. Preferably, the VCSEL chips 260 in each strip 252 would be electrically connected in series. The leads 260 are electrically connected to a controller/power supply circuit, as discussed above with respect to the previous embodiments.

In operation, the device is inserted directly into the coronary artery or directly into the patient's heart. Inflation fluid is provided through the inflation lumen 230 to the balloon 235. As the balloon 235 fills with fluid, it gradually expands to open the coronary artery. While the balloon 235 is expanded, the device is activated to provide power to the controller/power supply circuit. The VCSELs contained in each VCSEL chip 260 emit a low power laser beam through the optically clear silicone sleeve 240. The low power laser energy stimulates the affected area to improve healing. In an embodiment in which a balloon is not included, each VCSEL chip 260 emits a low power laser beam that passes directly to the internal surface of the artery or the heart. Alternatively, the device may be used external to an artery and inserted directly into the chest cavity during open heart surgery to irradiate an external surface of the heart, or may be inserted through the chest cavity into an artery that has been opened in the course of a bypass surgery.

Having thus described a preferred embodiment of a laser treatment device, it should be apparent to those skilled in the art that certain advantages of the within system have been achieved. It should also be appreciated that various mnodifications, adaptations, and alternative embodiments thereof may be made within the scope and spirit of the present invention. For example, VCSELs have been illustrated, but it should be apparent that the inventive concepts described above would be equally applicable using standard laser diodes or defocused surgical lasers, such as $CO_2$ lasers at low power densities. The invention is further defined by the following claims.

What is claimed is:

1. An apparatus for performing laser biostimulation therapy comprising: means for emitting at least one beam of laser energy; and a catheter comprising
    a housing having a main lumen defined within an inner edge of said housing,
    an inflatable balloon surrounding said housing and communicating with said main lumen,
    means for inflating said balloon coupled to said main lumen,
    a flexible sleeve surrounding said balloon, and
    at least one electrically conductive strip embedded within said flexible sleeve, said emitting means disposed on a surface of said at least one electrically conductive strip.

2. The apparatus of claim 1, wherein said emitting means further comprises at least one VCSEL operatively connected with said controlling means for generating said at least one beam of laser energy.

3. The apparatus of claim 1, further comprising means for storing a treatment regimen for the apparatus, said storing means being operatively connected to said controlling means.

4. The apparatus of claim 1, wherein said controlling means is programmable.

5. The apparatus of claim 1, wherein said flexible sleeve is comprised of an optically transparent material.

6. The apparatus of claim 1, wherein said optically transparent material is comprised of soft silicone.

7. The apparatus of claim 1, wherein said flexbile sleeve has a thickness in a range of approximately 0.25 to 0.50 millimeters.

* * * * *

UNITED STATES PATENT AND TRADEMARK OFFICE
CERTIFICATE OF CORRECTION

PATENT NO. : 5.989,245
DATED : November 23, 1999
INVENTOR(S) : Marvin A. Prescott It is certified that error appears in the above-identified patent and that said Letters Patent is hereby corrected as shown below:

Replace at cover page, column one, item [63]:

"[63] Continuation-in-part of application No. 08/215,263, Mar. 21, 1994, Pat. No. 5,616,140, which is a continuation-in-part of application No. 08/703,488, Aug. 26, 1996, Pat. No. 5,814,039."

with:

-- [63] Continuation-in-part of application No. 08/215,263, Mar. 21, 1994, Pat. No. 5,616,140, which is a continuation-in-part of application No. 08/703,422, Aug. 26, 1996, Pat. No. 5,814,039, which is a continuation-in-part of application No. 08/632,630, Apr. 15, 1996, Pat. No. 5,741,246. --

Replace at column 6, line 46:

"switch 16"

with:

-- switch 15 --

Signed and Sealed this

First Day of August, 2000

*Attest:*

*Attesting Officer*

Q. TODD DICKINSON

*Director of Patents and Trademarks*